United States Patent [19]

Nakao et al.

[11] Patent Number: 5,045,541
[45] Date of Patent: Sep. 3, 1991

[54] FUSED PYRIDAZINE COMPOUNDS AND THEIR PHARMACEUTICAL USE

[75] Inventors: Toru Nakao, Nakatsu; Minoru Kawakami, Fukuoka; Masao Hisadome; Tetsuya Tahara, both of Nakatsu, all of Japan

[73] Assignee: Yoshitomi Pharmaceutical Industries, Ltd., Osaka, Japan

[21] Appl. No.: 391,603

[22] PCT Filed: Oct. 29, 1988

[86] PCT No.: PCT/JP88/01109

§ 371 Date: Jul. 2, 1989

§ 102(e) Date: Jul. 2, 1989

[87] PCT Pub. No.: WO89/04306

PCT Pub. Date: May 18, 1989

[30] Foreign Application Priority Data

Nov. 2, 1987 [JP] Japan .................. 62-278099
Sep. 30, 1988 [JP] Japan .................. 63-248295

[51] Int. Cl.$^5$ .................. A61K 31/50; C07D 487/04; C07D 403/04; C07D 237/36
[52] U.S. Cl. .................. 514/248; 514/232.5; 514/232.8; 544/115; 544/234; 546/269; 546/274; 546/297; 549/23; 549/401; 549/404; 562/440; 562/461
[58] Field of Search .................. 514/248, 232.5, 232.8; 544/234, 115

[56] References Cited

U.S. PATENT DOCUMENTS 4,602,019 7/1986 Sircar et al. .................. 544/234
4,692,447 9/1987 Cignarella et al. .................. 544/234
4,755,511 7/1988 Warrington .................. 544/234
4,843,075 6/1989 Nakao et al. .................. 544/234
4,849,421 7/1989 Nakao et al. .................. 544/234

FOREIGN PATENT DOCUMENTS 9991 1/1989 Japan .
2185977 3/1986 United Kingdom .

Primary Examiner—Mukund J. Shah
Assistant Examiner—E. Bernhardt
Attorney, Agent, or Firm—Wenderoth, Lind & Ponack

[57] ABSTRACT

Fused pyridazine compounds

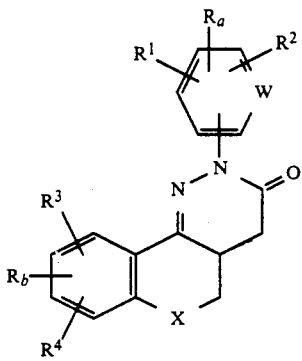

wherein $R^1$, $R^2$, $R^3$ and $R^4$ are the same or different and respectively hydrogen, a halogen, hydroxy, nitro, amino, cyano, trifluoromethyl, and alkyl, an alkoxy or an alkanoylamino; one of $R_a$ and $R_b$ is a group of the formula $$-O-Y-NR^5R^6$$

wherein $R^5$ and $R^6$ are the same or different and respectively hydrogen, an alkyl, a phenylalkyl or a substituted phenylalkyl or a group forming a heterocycle together with the adjacent nitrogen atom and Y stands for a straight- or branched-chain alkylene which may have hydroxy group as a substituent on the chain, and the other is hydrogen, or both of $R_a$ and $R_b$ are the same or different and respectively a group of the formula $$-O-Y-NR^5R^6$$

wherein $R^5$ and $R^6$ are of the same meanings as defined above; W is $=CH-$ or $=N$; X is $CH_2$, S, SO, $SO_2$ or O; and the bond designated by a broken line in its part stands for a single bond or a double bond, or their pharmaceutically acceptable salts or hydrates and their pharmaceutical use.

Said compounds possess stimulating effects on phagocytosis of leukocytes and macrophages, restorative effects on leukopenia, protective effects against infection, antitumor actions and the like and thus they are useable for the prophylaxis or therapy of human diseases accompanied by immunodeficiency.

4 Claims, No Drawings

FUSED PYRIDAZINE COMPOUNDS AND THEIR PHARMACEUTICAL USE

TECHNICAL FIELD

This invention relates to fused pyridazine compounds or their pharmaceutically acceptable salts or hydrates and the pharmaceutical use.

BACKGROUND ART

Heretofore, there have been known 8-amino-4,4a,5,6-tetrahydro-2H-benzo[h]cinnolin-3-one possessing platelet aggregation-suppressing actions, vasodilating actions, antiulcer actions and so on in Japanese Patent Application Laid-open (Kokai) No. 47468/1986; benzo[h]cinnoline derivatives possessing anxiolytic actions, platelet aggregationsuppressing actions, diuretic actions and antidotal actions against administration of an excessive amount of anxiolytics in Kokai No. 56169/1986; benzothiopyrano[4,3-c]pyridazine compounds possessing anxiolytic actions or antidotal actions against administration of an excessive amount of anxiolytics in W087/04162 and (1)benzopyrano[4,3-c]pyridazin-3-one compounds in Bulletin of the Chemical Society of Japan, vol. 55, pp. 2450–2455 (1982) respectively as fused pyridazine compounds exhibiting pharmacological activities.

Meanwhile, there is a growing trend toward increase of human diseases which are caused by disorders in immune function such as autoimmunity diseases, infectious diseases, immuno-deficiency diseases and so on.

It is known that an adrenal cortical hormone which is one of the widely-used therapeutic medicines for the immune disorder diseases exhibits a drastic effect thereon, while it brings about serious side effects such as immune function deficiency, infectious diseases and edema.

The object of this invention resides in providing compounds with low level of side effects, which are useful for the prophylaxis and therapy of various diseases associated with immune function deficiency.

DISCLOSURE OF INVENTION

As a result of the present inventors' studies, they found that the fused pyridazine compounds having aminoalkoxy substituents exhibited not only excellent immune functionimproving actions but also infectionphylactic actions and antitumor actions, and besides have few side effects and are extremely safe in the aspect of toxicities, which resulted in the completion of this invention.

This invention relates to the fused pyridazine compounds of the general formula

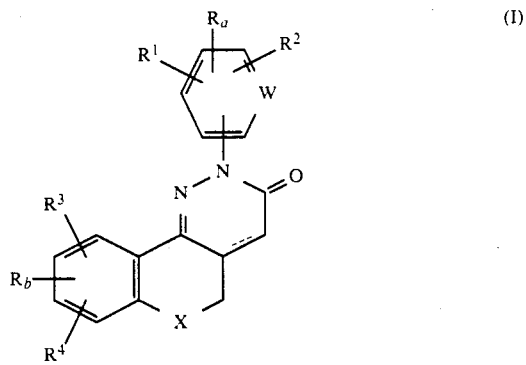

wherein $R^1$, $R^2$, $R^3$ and $R^4$ are the same or different and respectively hydrogen, a halogen, hydroxy, nitro, amino, cyano, trifluoromethyl, an alkyl, an alkoxy or an alkanoylamino; one of $R_a$ and $R_b$ is a group of the formula $$-O-Y-NR^5R^6$$

wherein $R^5$ and $R^6$ are the same or different and respectively hydrogen, an alkyl or a phenylalkyl or a substituted phenylalkyl a group forming a heterocycle together with the adjacent nitrogen atom and Y stands for a straight- or branched-chain alkylene which may have hydroxy group as a substituent on the chain, and the other is hydrogen, or both of $R_a$ and $R_b$ are the same or different and respectively a group of the formula $$-O-Y-NR^5R^6$$

wherein $R^5$ and $R^6$ are of the same meanings as defined above; W is $=CH-$ or $=N-$; X is $CH_2$, S, SO, $SO_2$ or O; and the bond designated by a broken line in its part stands for a single bond or a double bond, or their pharmaceutically acceptable salts or hydrates and their pharmaceutical uses.

Throughout the present specification, the halogen means chlorine, bromine, fluorine or iodine; the alkyl means straight- or branched-chain alkyl having 1–8 carbon atoms such as methyl, ethyl, propyl, isopropyl, butyl, isobutyl, tert-butyl, pentyl, hexyl, heptyl or octyl; the alkoxy means a straight- or branched-chain alkoxy having 1–8 carbon atoms such as methoxy, ethoxy, propoxy, isopropoxy, butoxy, isobutoxy, tert-butoxy, pentyloxy, hexyloxy or octyloxy; the phenylalkyl means a phenylalkyl in which the alkyl moiety is a straight- or branched-chain having 1–4 carbon atoms such as benzyl, 1-phenylethyl, 2-phenylethyl, 3-phenylpropyl or 4-phenylbutyl; the substituted phenylalkyl is a phenylalkyl having, on the phenyl ring, 1 to 3 substituent(s) selected from halogens, hydroxy, nitro, amino, cyano, trifluoromethyl, alkyls, alkoxys and alkanoylaminos; the heterocyclic group formed together with the adjacent nitrogen atom means a 5- or 6-membered heterocyclic group such as 1-pyrrolidinyl, piperidino, morpholino, 1-piperazinyl, 4-substituted-1-piperazinyl (the substituent being an alkyl, a hydroxyalkyl, a phenylalkyl, a substituted phenylalkyl, phenyl or a substituted phenyl); the alkylene means a straight- or branched-chain alkylene having 1–8 carbon atoms such as methylene, ethylene, trimethylene, tetramethylene, propylene, hexamethylene or octamethylene; the hydroxy-substituted alkylene means 1-hydroxyethylene, 1-hydroxytrimethylene or 2-hydroxytrimethylene; the alkanoylamino means an alkanoylamino having 2-5 carbon atoms such as acetylamino, propionylamino, butyrylamino, pivaloylamino or valerylamino.

As the pharmaceutically acceptable salts of the compounds of the general formula (I), mention is made of acid addition salts of inorganic acids (hydrochloric acid, hydrobromic acid, sulfuric acid, nitric acid, phosphoric acid, etc.) or organic acids (maleic acid, fumaric acid, malic acid, succinic acid, citric acid, tartaric acid, acetic acid, lactic acid, methanesulfonic acid, p-toluenesulfonic acid, pamoic acid, etc.) or their quaternary salts. As the hydrates thereof, mention is made of monohydrate, hemihydrate, sesquihydrate, dihydrate and the like.

When the compounds (I) of the present invention have an asymmetric carbon atom, they can be obtained as the racemic mixtures or the optically active isomers. When the compounds (I) have at least two asymmetric carbon atoms, they can be obtained as the individual diastereomers or the mixtures thereof. The present invention encompasses these mixtures and their individual isomers. This invention also encompasses stereoisomers.

As the preferable compounds of this invention, there may be mentioned the compounds of the general formula (I) wherein $R_a$ is $-O-Y-NR^5R^6$ and $R_b$ is hydrogen or their pharmaceutically acceptable salts or hydrates, more preferably the compounds of said compounds wherein X is $CH_2$ or S. As the particularly preferable compounds of the present invention, mention may be made of 9-fluoro-2-[4-(2-dimethylaminopropoxy)phenyl]-5,6-dihydrobenzo[h]cinnolin-3(2H)-one, 9-fluoro-2-[4-(1-methyl-2-dimethylaminoethoxy)phenyl]-4,4a,5,6-tetrahydrobenzo[h]cinnolin-3(2H)-one, 9-fluoro-2-[4-(2-methylaminopropoxy)phenyl]-5,6-dihydrobenzo[h]cinnolin-3(2H)-one, 9-fluoro-2-[4-(3-dimethylaminopropoxy)phenyl]-4,4a,5,6-tetrahydrobenzo[h]cinnolin-3(2H)-one, 2-[4-(3-dimethylaminopropoxy)phenyl]-2,3,4,4a-tetrahydro-5H-(1)benzothiopyrano[4,3-c]pyridazin-3-one, 9-fluoro-2-[3-(3-dimethylaminopropoxy)phenyl]-4,4a,5,6-tetrahydrobenzo[h]cinnolin-3(2H)-one, 9-fluoro-2-[3-(2-methyl-3dimethylaminopropoxy)phenyl]-4,4a,5,6-tetrahydrobenzo[h]-cinnolin-3(2H)-one, 2-[4-(2-diethylaminoethoxy)phenyl]-2,3,4,4a-tetrahydro-5H-(1)benzothiopyrano[4,3-c]pyridazin-3-one and 9-fluoro-2-[4-(2-hydroxy-3-isopropylaminopropoxy)phenyl]-4,4a,5,6-tetrahydrobenzo[h]cinnolin-3(2H)-one and their pharmaceutically acceptable salts and hydrates.

The compounds of the general formula (I) in the present invention can be synthesized, for example, by the following methods.

Method (1)

A method which comprises reacting a compound of the general formula

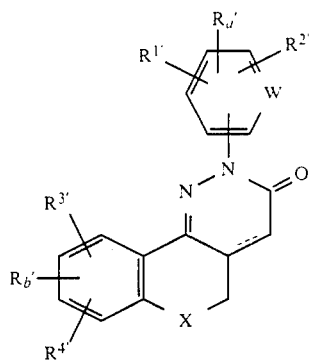

wherein one of $R_a'$ and $R_b'$ is hydrogen or a group of the formula:

$$-Y-NR^5R^6$$

and the other is hydroxy, or both mean hydroxy; $R^{1'} R^{2'}$, $R^{3'}$ and $R^{4'}$ mean a substituent or an atom as defined above for $R^1$, $R^2$, $R^3$ and $R^4$ respectively except hydroxy; and the other symbols are as defined above, with a compound of the general formula $$Q-Y-NR^5R^6 \quad (III)$$

wherein Q is a halogen or an active ester of an alcohol such as methanesulfonyloxy or p-toluenesulfonyloxy and the other symbols are respectively as defined above.

The reaction usually proceeds in a suitable solvent (an alcohol such as methanol, ethanol or isopropyl alcohol, benzene, toluene, xylene, tetrahydrofuran, dimethylformamide, dimethylacetamide, etc.) in the presence of a deacidifying agent (sodium methoxide, sodium ethoxide, sodium hydride, sodium amide, sodium hydroxide, potassium hydroxide, potassium carbonate, sodium carbonate, etc.) at room temperature or under reflux of the solvent used in 1–20 hours.

Method (2)

A method which comprises reacting a compound of the general formula

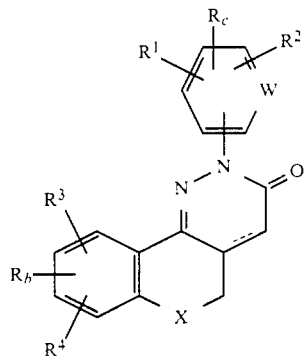

wherein one of $R_c$ and $R_d$ is 2,3-epoxypropoxy and the other is hydrogen, or both of them are 2,3-epoxypropoxy and the other symbols are as defined above, with an amine compound of the general formula $$HNR^5R^6 \quad (V)$$

wherein each of the symbols is as defined above. The reaction usually proceeds in a suitable solvent (an alcohol such as methanol, ethanol or isopropyl alcohol, dimethylformamide and dimethylacetamide, etc.) at room temperature or under reflux of the used solvent in 1–20 hours.

Method (3)

A method which comprises reacting a compound of the general formula

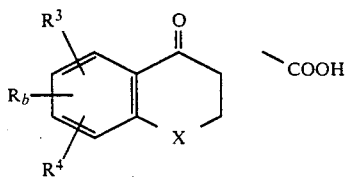

wherein each of the symbols is as defined above, with a hydrazine compound of the general formula

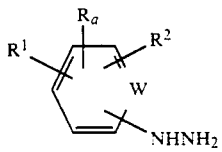

wherein each of the symbols is as defined above, or a hydrate or an acid addition salt thereof to give a compound of the general formula

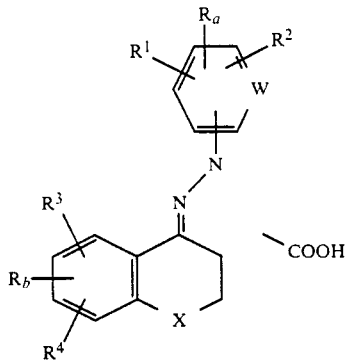

wherein each of the symbols is as defined above, which is subjected to ring-closure reaction.

The reaction usually proceeds in a suitable solvent (an alcohol such as methanol, ethanol or propanol) while heating under reflux for 5–20 hours to yield a compound of the general formula (I) or a compound of the general formula (VIII).

When the hydrazine derivative of the general formula (III) is an acid addition salt, the reaction is conducted in the presence of an deacidifying agent (sodium acetate, potassium acetate, sodium hydrogencarbonate, sodium carbonate, potassium carbonate, etc.). When a compound of the general formula (VIII) is obtained, the corresponding compound of the general formula (I) can be prepared by heating under reflux in acetic acid for 5–10 hours.

Method (4)

In the case of a compound of the general formula (I) wherein $R_a$ stands for $-O-Y-NR^5R^6$:

A method which comprises reacting a compound of the general formula

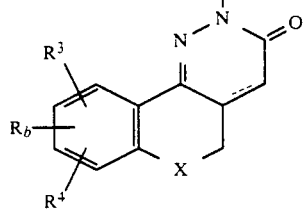

wherein $R^7$ is hydrogen or alkyl, Z is a straight- or branched-alkylene and the other symbols are as defined above, with a compound of the general formula (V) or an acid addition salt thereof under reductive conditions or subjecting the condensed product thereof to reduction reaction to produce a compound of the general formula

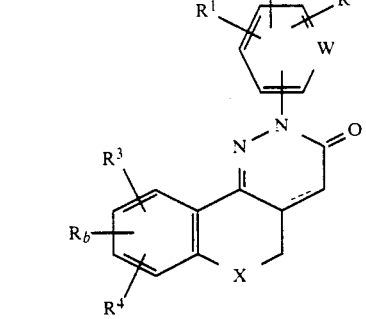

wherein each of the symbols is as defined above.

The reaction preferably proceeds by reducing a compound (IX) and an acid addition salt of a compound (V) in an alcohol solvent (methanol, ethanol, etc.) under ice-cooling to under reflux of the solvent used with a reducing agent (sodium cyanoborohydride, etc.), or by condensing a compound (IX) and a compound (V) in a suitable solvent to give the product (the Schiff base or enamine compound), followed by reduction of the product with a reducing agent (sodium borohydride, etc.). In the latter case, when an alcohol solvent is used as the solvent, the reaction is preferably conducted by keeping the mixture under reflux of the used solvent for 1–20 hours and then adding a reducing agent under ice-cooling. When benzene, toluene or the like is used as the solvent, the mixture is preferably heated under reflux for 1–20 hours, concentrated under reduced pressure and then dissolved in, for example, methanol, followed by addition of a reducing agent under ice-cooling. In the case of a compound of the general formula (IX) wherein X is $CH_2$ or O, the reaction proceeds by catalytic reduction under atmospheric pressure of hydrogen in the presence of a catalyst such as palladiumcarbon in a solvent such as ethanol in an autoclave. A compound (IX) can be subjected to the reaction in the form of the acetal.

Method (5)

In the case of a compound of the general formula (I) wherein X is SO or $SO_2$:

A method which comprises subjecting a compound of the general formula (I) wherein X is S to oxidation reaction to give the corresponding compound of the general formula (I) wherein X is SO or $SO_2$.

The reaction proceeds by keeping the starting compound in a suitable solvent in the presence of an oxidizing agent (peroxyacetic acid, peroxybenzoic acid, meta-chloroperoxybenzoic acid, sodium hypobromide, etc.) at a temperature ranging from 0° C. to 100° C. for 1–10 hours. When the reaction is conducted by keeping in acetic acid as the solvent in the presence of hydrogen peroxide at room temperature for 1–5 hours, a compound of the general formula (I) wherein X is SO can be obtained dominantly. A compound of the general formula (I) wherein X is $SO_2$ can be obtained by keeping at 30°–100° C. for 2–10 hours.

Method (6)

In the case of a compound of the formula (I) wherein the bond in the portion indicated by a broken line is a double bond, the compound can be prepared by adding dropwise to the corresponding compound of the general formula (I) wherein the bond is a single bond bromine in a 1–1.5 times molar amount at 20°–60° C. in the presence of acetic acid [Journal of Medicinal Chemistry, vol. 14, p. 262 (1971)]or by the method which comprises reacting with sodium m-nitrobenzenesulfonate (Bachmann Method, British Patent No. 1168291).

Method (7)

A method which comprises converting a substituent of a group of $R^1$, $R^2$, $R^3$ or $R^4$ of a compound obtained in accordance with the above-mentioned Methods (1) to (6) to another group by a conventional organic chemical means.

As such means, for example, mention is made of a method which comprises reducing nitro group to amino group, a method which comprises subjecting amino group to lower-alkanoylation, a method which comprises converting amino group to cyano group (Sandmeyer's Reaction, Gattermann Reaction) and the like.

Method (8)

A quaternary salt can be obtained by, for example, dissolving a compound obtained in accordance with the above-mentioned Methods (1) to (7) in acetone, adding an excessive amount of methyl iodide thereto and heating for 1–3 hours.

The compounds of the present invention obtained in accordance with the above-mentioned Methods (1) to (7) can be converted into an inorganic salt thereof such as hydrochloride, hydrobromide, sulfate, phosphate and so on or an organic salt thereof such as maleate, fumarate, malate, succinate, citrate, tartarate, acetate, lactate, methanesulfonate, p-toluenesulfonate or pamoate by treating them with an inorganic acid or an organic acid as mentioned above.

Racemic mixtures can be resolved into the desired optical isomers by means of fractional recrystallization of a salt of an optically active acid or by passing them into a column filled with an optically active carrier. The individual diastereomers can be separated by a means such as fractional crystallization, chromatography or the like. The optically active isomers can be obtained by employing the optically active starting compounds.

The stereoisomers can be isolated by a method such as recrystallization method or column chromatography method.

As the examples of the compounds (I) of this invention, mention may be made of the following compounds besides the compounds mentioned below in working Examples.

2-[4-(1-Methyl-2-dimethylaminoethoxy)phenyl]-4,4a,5,6-tetrahydrobenzo[h]cinnolin-3(2H)-one 2-[4-(1-Methyl-2-dimethylaminoethoxy)phenyl]-5,6-dihydrobenzo[h]cinnolin-3(2H)-one 2-[4-( aminopropoxy)phenyl]-4,4a,5,6-tetrahydrobenzo[h]cinnolin-3(2H)-one 2-[4-(2-Methyl-3-dimethylaminopropoxy)phenyl]-5,6-dihydrobenzo[h]cinnolin-3(2H)-one 2-[4-(3-(1-pyrrolidinyl)propoxy)phenyl]-4,4a,5,6-tetrahydrobenzo[h]cinnolin-3(2H)-one 2-[4-(3-(4-Methyl-1-piperazinyl)propoxy)phenyl]-4,4a,5,6-tetrahydrobenzo[h]cinnolin-3(2H)-one 2-[4-(3-Thiomorpholinopropoxy)phenyl]-4,4a,5,6-tetrahydrobenzo[h]cinnolin-3(2H)-one 2-[4-(1-Methyl-2-trimethylammonioethoxy)phenyl]-4,4a,5,6-tetrahydrobenzo[h]cinnolin-3(2H)-one·iodide 2-[4-(1-Methyl-2-trimethylammonioethoxy)phenyl]-5,6-dihydrobenzo[h]cinnolin-3(2H)-one·iodide 2-(4-Methylphenyl)-9-(1-methyl-2-dimethylaminoethoxy)-4,4a,5,6-tetrahydrobenzo[h]cinnolin-3(2H)-one 2-(4-Methylphenyl)-9-(1-methyl-2-dimethylaminoethoxy)-5,6-dihydrobenzo[h]cinnolin-3(2H)-one 2-(4-Methylphenyl)-9-(1-methyl-2-trimethylammonioethoxy)-5,6-dihydrobenzo[h]cinnolin-3(2H)-one·iodide 2-(4-Methylphenyl)-9-(2-methyl-3-dimethylaminopropoxy)-4,4a,5,6-tetrahydrobenzo[h]cinnolin-3(2H)-one 9-Methoxy-2-[4-(1-methyl-2-dimethylaminoethoxy)phenyl]-5,6-dihydrobenzo[h]cinnolin-3(2H)-one 2-(4-Methoxyphenyl)-9-(1-methyl-2-dimethylaminoethoxy)-5,6-dihydrobenzo[h]cinnolin-3(2H)-one 2-[4-(1-Methyl-2-dimethylaminoethoxy)phenyl]-9-(1-methyl-2-dimethylaminoethoxy)-5,6-dihydrobenzo[h]cinnolin-3(2H)-one 2-[4-(1-Methyl-3-dimethylaminopropoxy)phenyl]-9-(2-methyl-3-dimethylaminopropoxy)-5,6-dihydrobenzo[h]cinnolin-3(2H)-one 2-(4-Fluorophenyl)-9-(2-hydroxy-3-isopropylaminopropoxy)-5,6-dihydrobenzo[h]cinnolin-3(2H)-one 9-(2-Hydroxy-3-isopropylaminopropoxy)-2-(4-methylphenyl)-5,6-dihydrobenzo[h]cinnolin-3(2H)-one 2-[4-(2-Hydroxy-3-isopropylaminopropoxy)phenyl]-9-(2-hydroxy-3-isopropylaminopropoxy)-5,6-dihydrobenzo[h]cinnolin-3(2H)-one 9-Chloro-2-[4-(1-methyl-2-dimethylaminoethoxy)phenyl]-5,6-dihydrobenzo[ h]cinnolin-3(2H)-one 9-Chloro-2-[4-(2-methyl-3-dimethylaminopropoxy)phenyl]-5,6-dihydrobenzo[h]cinnolin-3(2H)-one 9-Chloro-2-[4-(1-methyl-2-dimethylaminoethoxy)phenyl]-4,4a,5,6-tetrahydrobenzo[h]cinnolin-3(2H)-one 9-Chloro-2-[4-(2-methyl-3-dimethylaminopropoxy)phenyl]-4,4a,5,6-tetrahydrobenzo[h]cinnolin-3(2H)-one 9-Methyl-2-[4-(1-methyl-2-dimethylaminoethoxy)-phenyl]-5,6-dihydrobenzo[h]cinnolin-3(2H)-one 9-Methyl-2-[4-(2-methyl-3-dimethylaminopropoxy)-phenyl]-5,6-dihydrobenzo[h]cinnolin-3(2H)-one 8,9-Dimethyl-2-[4-(1-methyl-2-dimethylaminoethoxy)-phenyl]-5,6-dihydrobenzo[h]cinnolin-3(2H)-one 8,9-Dimethyl-2-[4-(2-methyl-3-dimethylaminopropoxy)phenyl]-5,6-dihydrobenzo[h]cinnolin-3(2H)-one 9-Fluoro-2-[4-(1-methyl-2-trimethylammonioethoxy)-phenyl]-5,6-dihydrobenzo[h]cinnolin-3(2H)-one·iodide 9-Fluoro-2-[4-(2-methyl-3-trimethylammoniopropoxy)-phenyl]-5,6-dihydrobenzo[h]cinnolin-3(2H)-one·iodide 9-Fluoro-2-[4-(2-hydroxy-3-isopropylaminopropoxy)-phenyl]-5,6-dihydrobenzo[h]cinnolin-3(2H)-one 2-[4-(3-tert-Butylamino-2-hydroxypropoxy)phenyl]-9-fluoro-5,6-dihydrobenzo[h]cinnolin-3(2H)-one 9-Fluoro-2-[4-(2-hydroxy-3-(1-pyrrolidinyl)propoxy)-phenyl]-5,6-dihydrobenzo[h]cinnolin-3(2H)-one 9-Fluoro-2-[4-(2-hydroxy-3-piperidinopropoxy)-phenyl]-5,6- dihydrobenzo[ h]cinnolin-3(2H)-one 9-Fluoro-2-[4-(2-hydroxy-3-morpholinopropoxy)-phenyl]-5,6-dihydrobenzo[h]cinnolin-3(2H)-one 9-Fluoro-2-[4-(2-hydroxy-3-(4-methyl-1-piperazinyl)-propoxy)phenyl]-5,6-dihydrobenzo[h]cinnolin-3(2H)-one 2-[4-(1-Methyl-2-dimethylaminoethoxy)phenyl]-2,3-dihydro-5H-(1)benzopyrano[4,3-c]pyridazin-3-one 2-[4-(2-Methyl-3-dimethylaminopropoxy)phenyl]-2,3-dihydro-5H-(1)benzopyrano[4,3-c]pyridazin-3-one 2-[4-(2-Hydroxy-3-isopropylaminopropoxy)phenyl]-2,3-dihydro-5H-(1)benzopyrano[4,3-c]pyridazin-3-one 2-[4-(3-tert-Butylamino-2-hydroxypropoxy)phenyl]-2,3-dihydro-5H-(1)benzopyrano[4,3-c]pyridazin-3-one 9-Methyl-2-[4-(1-methyl-2-dimethylaminoethoxy)-phenyl]-2,3-dihydro-5H-(1)benzopyrano[4,3-c]pyridazin-3-one 9-Methyl-2-[4-(2-methylaminopoxy)phenyl]-2,3-dihydro-5H-(1)benzopyrano[4,3-c]pyridazin-3-one 9-Fluoro-2-[4-(1-methyl-2-dimethylaminoethoxy)-phenyl]-2,3-dihydro-5H-(1)benzopyrano[4,3-c]pyridazin-3-one 9-Fluoro-2-[4-(2-methyl-3-dimethylaminopropoxy)-phenyl]-2,3-dihydro-5H-(1)benzopyrano[4,3-c]pyridazin-3-one 2-(4-Methylphenyl)-8(1-methyl-2-dimethylaminoethoxy)-4,4a,5,6-tetrahydrobenzo[h]cinnolin-3(2H)-one 2-(3-Methylphenyl)-8-(1-methyl-2-dimethylaminoethoxy)-4,4a,5,6-tetrahydrobenzo[h]cinnolin-3(2H)-one 2-(2-Methylphenyl)-8-(1-methyl-2-dimethylaminoethoxy)-4,4a,5,6-tetrahydrobenzo[h]cinnolin-3(2H)-one 9-Hydroxy-2-[4-(1-methyl-2-dimethylaminoethoxy)-phenyl]-5,6-dihydrobenzo[h]cinnolin-3(2H)-one 2-(4-Hydroxyphenyl)-9-(1-methyl-2-dimethylaminoethoxy)-5,6-dihydrobenzo[h]cinnolin-3(2H)-one 2-(3,4-Dichlorophenyl)-9-(1-methyl-2-dimethylaminoethoxy)-5,6-dihydrobenzo[h]cinnolin-3(2H)-one 9-(1-methyl-2-dimethylaminoethoxy)-2-(2-pyridyl)-5,6-dihydrobenzo[h]cinnolin-3(2H)-one 9-(1-methyl-2-dimethylaminoethoxy)-2-(4-pyridyl)-5,6-dihydrobenzo[h]cinnolin-3(2H)-one 8-(2-Diethylaminoethoxy)-2-(2-pyridyl)-4,4a,5,6-tetrahydrobenzo[h]cinnolin-3(2H)-one 8-(3-Dimethylaminopropoxy)-2-(2-pyridyl)-4,4a,5,6-tetrahydrobenzo[h]cinnolin-3(2H)-one 8-(3-Morpholinopropoxy)-2-(2-pyridyl)-5,6-dihydrobenzo[h]cinnolin-3(2H)-one 8-(3-Dimethylaminopropoxy)-2-(2-pyridyl)-5,6-dihydrobenzo[h]cinnolin-3(2H)-one 9-Fluoro-2-[3-(2-dimethylaminoethoxy)-2-pyridyl]-4,4a,5,6-tetrahydrobenzo[h]cinnolin-3(2H)-one 9-Fluoro-2-[3-(3-dimethylaminopropoxy)-2-pyridyl]-4,4a,5,6-tetrahydrobenzo[h]cinnolin-3(2H)-one 2-[4-(1-Methyl-2-dimethylaminoethoxy)phenyl]-2,3-dihydro-5H-(1)benzothiopyrano[4,3-c]pyridazin-3-one 2-[4-(2-Methyl-3-dimethylaminopropoxy)phenyl]-2,3,4,4a-tetrahydro- 5H-(1)benzothiopyrano[4,3-c]pyridazin-3-one 2-[4-(2-Methyl-3-dimethylaminopropoxy)phenyl]-2,3-dihydro-5H-(1)benzothiopyrano[4,3-c]pyridazin-3-one 2-[4-(1-Methyl-2-dimethylaminoethoxy)phenyl]-2,3,4,4a-tetrahydro-5H-(1)benzothiopyrano[4,3-c]pyridazin-3-one.6-oxide 2-[4-(1-Methyl-2-dimethylaminoethoxy)phenyl]-2,3-dihydro-5H-(1)benzothiopyrano[4,3-c]pyridazin-3-one.6-oxide 2-[4- inoethoxy)phenyl]-2,3-dihydro-5H-(1)benzothiopyrano[4,3-c]pyridazin-3-one.6,6-dioxide 2-[4-(1-Methyl-2-trimethylammonioethoxy)phenyl]-2,3-dihydro-5H-(1)benzothiopyrano[4,3-c]pyridazin-3-one·iodide 2-[4-(1-Methyl-2-trimethylammonioethoxy)phenyl]-2,3-dihydro-5H-(1)benzothiopyrano[4,3-c]pyridazin-3-one.6-oxide.iodide 9-Fluoro-2-[4-(1-methyl-2-dimethylaminoethoxy)-phenyl]-2,3,4,4a-tetrahydro-5H-(1)benzothiopyrano[4,3-c]pyridazin-3-one 9-Fluoro-2-[4-(1-methyl-2-dimethylaminoethoxy)-phenyl]-2,3-dihydro-5H-(1)benzothiopyrano[4,3-c]pyridazin-3-one 9-Fluoro-2-[4-(1-methyl-2-dimethylaminoethoxy)-phenyl]-2,3,4,4a-tetrahydro-5H-(1)benzothiopyrano[4,3-c]pyridazin-3-one.6-oxide 9-Fluoro-2-[4-(1-methyl-2-dimethylaminoethoxy)-phenyl]-2,3-dihydro-5H-(1)benzothiopyrano[4,3-c]pyridazin-3-one.6-oxide 9-Fluoro-2-[4-(2-hydroxy-3-dimethylaminopropoxy)-phenyl]-2,3,4,4a-tetrahydro-5H-(1)benzothiopyrano[4,3-c]pyridazin-3-one 9-Fluoro-2-[4-(2-hydroxy-3-dimethylaminopropoxy)-phenyl]-2,3-dihydro-5H-(1)benzothiopyrano[4,3-c]pyridazin-3-one 7-Chloro-2-[4-(1-methyl-2-dimethylaminoethoxy)-phenyl]-2,3,4,4a-tetrahydro-5H-(1)benzothiopyrano[4,3-c]pyridazin-3-one 7-Chloro-2-[4-(1-methyl-2-dimethylaminoethoxy)-phenyl]-2,3-dihydro-5H-(1)benzothiopyrano[4,3-c]pyridazin-3-one 9-Methyl-2-[4-(1-methyl-2-dimethylaminoethoxy)-phenyl]-2,3,4,4a-tetrahydro-5H-(1)benzothiopyrano[4,3-c]pyridazin-3-one 9-Methyl-2-[4-(1-methyl-2-dimethylaminoethoxy)-phenyl]-2,3-dihydro-5H-(1)benzothiopyrano[4,3-c]pyridazin-3-one 2-(4-Methylphenyl)-9-(1-methyl-2-dimethylaminoethoxy)-2,3,4,4a-tetrahydro-5H-(1)benzothiopyranoethoxy)phenyl]-9-(1-methyl-2-dimethylaminoethoxy)-2,3-dihydro-5H-(1)benzothiopyrano[4,3-c]pyridazin-3-one 2-(4-Chlorophenyl)-9-(1-methyl-2-dimethylaminoe-
  thoxy)-2,3-dihydro-5H-(1)benzothiopyrano[4,3-
  c]pyridazin-3-one
2-(4-Methylphenyl)-9-(1-methyl-2-dimethylaminoe-
  thoxy)-2,3-dihydro-5H-(1)benzothiopyrano[4,3-
  c]pyridazin-3-one
2-(4-Fluorophenyl)-9-(2-methyl-3-dimethylamino-
  propoxy)-2,3-dihydro-5H-(1)benzothiopyrano[4,3-
  c]pyridazin-3-one
2-(4-Methoxyphenyl)-9-(1-methyl-2-dimethylaminoe-
  thoxy)-2,3-dihydro-5H-(1)benzothiopyrano[4,3-
  c]pyridazin-3-one
9-Methyl-2-[4-(3-morpholinopropoxy)phenyl]-2,3,4,4a-
  tetrahydro-5H-(1)benzopyrano[4,3-c]pyridazin-3-one
2-[4-(3-Dimethylaminopropoxy)phenyl-2,3,4,4a-tet-
  rahydro-   5H-(1)benzothiopyrano[4,3-c]pyridazin-
  3-one
9-Fluoro-2-[4-(2-piperidinopropoxy)phenyl]-4,4a,5,6-
  tetrahydrobenzo[h]cinnolin-3(2H)-one
9-Fluoro-2-[4-(2-piperidinopropoxy)phenyl]-5,6-dihy-
  drobenzo[h]cinnolin-3(2H)-one
9-Fluoro-2-[4-(2-morpholinopropoxy)phenyl]-4,4a,5,6-
  tetrahydrobenzo[h]cinnolin-3(2H)-one
9-Fluoro-2-[4-(2-morpholinopropoxy)phenyl]-5,6-dihy-
  drobenzo[h]cinnolin-3(2H)-one
9-Fluoro-2-[4-(2-(4-methyl-1-piperazinyl)propoxy)-
  phenyl]-4,4a,5,6-tetrahydrobenzo[h]cinnolin-
  3(2H)-one
9-Fluoro-2-[4-(2-(4-methyl-1-piperazinyl)propoxy)-
  phenyl]-5,6-dihydrobenzo[h]cinnolin-3(2H)-one
9-Fluoro-2-[4-(2-isopropylaminopropoxy)phenyl]-
  4,4a,5,6-tetrahydrobenzo[h]cinnolin-3(2H)-one
9-Fluoro-2-[4-(2-isopropylaminopropoxy)phenyl]-5,6-
  dihydrobenzo[h]cinnolin-3(2H)-one
9-Fluoro-2[4-(2-(2-piperidinoethylamino)propoxy)-
  phenyl]-4,4a,5,6-tetrahydrobenzo[h]cinnolin-
  3(2H)-one
9-Fluoro-2-[4-(2-(2-piperidinoethylamino)propoxy)-
  phenyl]-5,6-dihydrobenzo[h]cinnolin-3(2H)-one
9-Fluoro-2-[4-(3-dimethylaminopropoxy)phenyl]-
  4,4a,5,6-tetrahydrobenzo[h]cinnolin-3(2H)-one
9-Fluoro-2-[4-(3-dimethylaminopropoxy)phenyl]-5,6-
  dihydrobenzo[h]cinnolin-3(2H)-one
2-[4-(2-Dimethylaminopropoxy)phenyl]-2,3-dihydro-
  5H-(1)benzothiopyrano[ 4,3-c]pyridazin-3-one
2-[4-(2-Dimethylaminopropoxy)phenyl]-2,3,4,4a-tet-
  rahydro-5H-(1)benzopyrano[4,3-c]pyridazin-3-one
2-[4-(2-Dimethylaminopropoxy)phenyl]-2,3-dihydro-
  5H-(1)benzopyrano[4,3-c]pyridazin-3-one
2-(4-Methylphenyl)-9-(2-dimethylaminopropoxy)-
  4,4a,5,6-tetrahydrobenzo[h]cinnolin-3(2H)-one
2-(4-Methylphenyl)-9-(2-dimethylaminopropoxy)-5,6-
  dihydrobenzo[h]cinnolin-3(2H)-one
2-(4-Methylphenyl)-9-(3-dimethylaminopropoxy)-5,6-
  dihydrobenzo[h]cinnolin-3(2H)-one
9-Fluoro-2-[3-(2-dimethylaminopropoxy)phenyl]-
  4,4a,5,6-tetrahydrobenzo[h]cinnolin-3(2H)-one
9-Fluoro-2-[3-(2-dimethylaminopropoxy)phenyl]-5,6-
  dihydrobenzo[h]cinnolin-3(2H)-one
9-Fluoro-2-[2-(2-dimethylaminopropoxy)phenyl]-
  4,4a,5,6-tetrahydrobenzo[h]cinnolin-3(2H)-one
9-Fluoro-2-[2-(2-dimethylaminopropoxy)phenyl]-5,6-
  dihydrobenzo[h]cinnolin-3(2H)-one The compounds of the general formula (IV) are novel. Among the compounds of the general formula (IV), for example, the compounds of the general formula

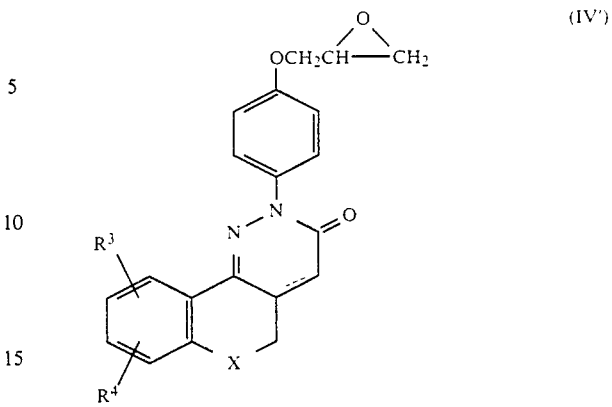

wherein each of the symbols is as defined above, can be obtained by treating the compounds of the general formula

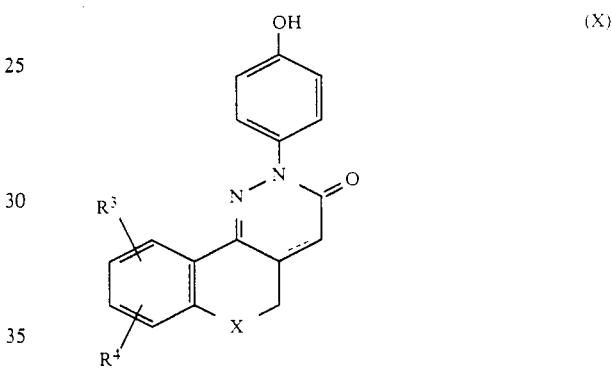

wherein each of the symbols is as defined above, with sodium hydroxide in methanol, followed by reaction with epichlorohydrin at 50°–55° C.

The compounds of the general formula (X) can be obtained, for example, by demethylation of the compounds of the general formula

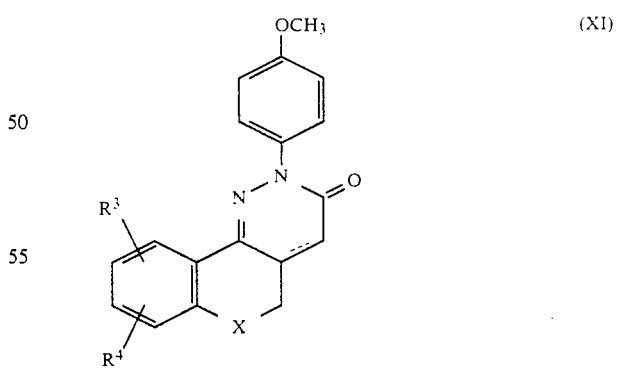

wherein each of the symbols is as defined above, with the use of 1-butanethiol-aluminium chloride or methionine-methanesulfonic acid in chloroform at room temperature.

The specific examples of the compounds of the general formula (IV′) and those of the general formula (X) are as follows, which are not limitative.

Examples of the compound (IV')

2-[4-(2,3-Epoxypropoxy)phenyl]-9-fluoro-4,4a,5,6-tetrahydrobenzo[h]cinnolin-2-one, m.p. 128°-130° C.

2-[4-(2,3-Epoxypropoxy)phenyl]-2,3,4,4a-tetrahydro-5H-(1)benzothiopyrano[4,3-c]pyridazin-3-one, m.p. 104°-106° C.

Examples of compound (X)

9-Fluoro-2-(4-hydroxyphenyl)-4,4a,5,6-tetrahydrobenzo[h]cinnolin-3(2H)-one, m.p. 285°-286° C. (decomposition)

9-Hydroxy-2-(4-hydroxyphenyl)-4,4a,5,6-tetrahydrobenzo[h]cinnolin-3(2H)-one, m.p. 280°-282° C. (decomposition)

9-Fluoro-2-(3-hydroxyphenyl)-4,4a,5,6-tetrahydrobenzo[h]cinnolin- 3(2H)-one, m.p. 210°-211° C.

9-Hydroxy-2-(4-methylphenyl)-4,4a,5,6-tetrahydrobenzo[h]cinnolin-3(2H)-one, m.p. 245°-246° C. (decomposition)

8-Hydroxy-2-(4-methylphenyl)-4,4a,5,6-tetrahydrobenzo[h]cinnolin-3(2H)-one, m.p. 275°-277° C. (decomposition)

8-Hydroxy-(3-methylphenyl)-4,4a,5,6-tetrahydrobenzo[h]cinnolin-3(2H)-one, m.p. 228°-230° C.

8,9-Dimethyl-2-(4-hydroxyphenyl)-4,4a,5,6-tetrahydrobenzo[h]cinnolin-3(2H)-one, m.p. 259°-260° C.

8-Hydroxy-2-(2-methylphenyl)-4,4a,5,6-tetrahydrobenzo[h]cinnolin-3(2H)-one, m.p. 215°-216° C. (decomposition)

9-Chloro-2-(4-hydroxyphenyl)-4,4a,5,6-tetrahydrobenzo[h]cinnolin-3(2H)-one, m.p. 279°-280° C. (decomposition)

9-Fluoro-2-(4-hydroxyphenyl)-5,6-dihydrobenzo[h]cinnolin-3(2H)-one, m.p. 300°-302° C. (decomposition)

9-Methyl-2-(4-hydroxyphenyl)-4,4a,5,6-tetrahydrobenzo[h]cinnolin-3(2H)-one 2-(2-Hydroxyphenyl)-4,4a,5,6-tetrahydrobenzo[h]cinnolin-3(2H)-one 2-(4-Hydroxyphenyl)-2,3,4,4a etrahydro-5H-(1)benzothiopyrano[4,3-c]pyridazin-3-one, m.p. 238°-240° C. (decomposition)

2-(3-Hydroxyphenyl)-2,3,4,4a-tetrahydro-5H-(1)benzothiopyrano[4,3-c]pyridazin-3-one, m.p. 221°-222° C.

9-Methyl-2-(4-hydroxyphenyl)-2,3,4,4a-tetrahydro-5H-(1)benzothiopyrano[4,3-c]pyridazin-3-one 2-(4-Chlorophenyl)-9-hydroxy-2,3,4,4a-tetrahydro-5H-( 1)benzothiopyrano[4,3-c]pyridazin-3-one 2-(4-Hydroxyphenyl)-2,3,4,4a-tetrahydro-5H-(1)benzothiopyrano[4,3-c]pyridazin-3-one 6-oxide The compounds of the general formula (IX) are novel compounds and they can be obtained, for example, by reacting the corresponding phenol compounds with a compound of the general formula

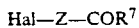  (XII)

wherein Hal is a halogen and the other symbols are as defined above, in a suitable solvent in the presence of a deacidifying agent (potassium carbonate, sodium carbonate, triethylamine, etc.).

In various pharmacological experiments using animals carrying diseases due to immunodeficiency, it was shown that the compounds of the present invention possess stimulating actions on phagocytosis of leukocytes, stimulating actions on phagocytosis of macrophages, restorative effects on leukopenia, infectionphylactic action, antitumor actions and so on. From these actions, it follows that the compounds of the present invention stimulate the function of reticuloendothelial system (RES) and activate immune responses. The compounds of the present invention are effectively applicable to human diseases associated with immunodeficiency. As diseases due to immunodeficiency, mention may be made of, for example, autoimmune diseases such as allergic diseases, lupus erythematosus, chronic articular rheumatism and the like, various infectious diseases due to the depression in immune function, and other hypoimmunity diseases in cancers and surgical operation. The compounds of the present invention can be used for the prophylaxis and therapy of the above-mentioned diseases.

The compounds of the present invention have low toxicity and can be safely administered to patients as pharmaceuticals.

The pharmaceutical composition containing a compound of the present invention as the active ingredient can be orally or non-orally administered as they are or in forms such as tablets, granules, powders, capsules, syrups, injections or preparations for external application which are obtained by mixing them with pharmaceutically acceptable carriers, excipients, diluents and the like.

While the dosage varies depending on age, bodyweight, symptom and so on of patients, for the therapy of human diseases associated with immunodeficiency such as autoimmune disorder and infectious diseases due to hypoimmunity, the daily dosage per an adult is usually in the range of about 0.5-100 mg, which can be administered at one dose or several divided doses.

Below, the present invention is concretely explained by illustrating Reference Examples and Working Examples, to which the present invention should not be limited.

REFERENCE EXAMPLE 1

To a solution of 5 g of methionine and 25 ml of methane-sulfonic acid is added 5 g of 9-fluoro-2-(4-methoxyphenyl)-5,6-dihydrobenzo[h]cinnolin-3(2H)-one. After the mixture is heated to 55° C. and stirred for 2 days, the reaction mixture is poured into water. The resulting crystals are collected and washed with ethanol to give 4.5 g of 9-fluoro-2-(4-hydroxyphenyl)-5,6-dihydrobenzo[h]cinnolin-3(2H)-one, m.p. 300°-302° C. (decomposition).

REFERENCE EXAMPLE 2

A mixture of 1.0 g of methionine, 70 ml of methanesulfonic acid and 10 g of 8-methoxy-2-(2-pyridyl)-4,4a,5,6-tetrahydrobenzo[h]cinnolin-3(2H)-one is stirred at 55° C. for 26 hours. The reaction mixture is poured into ice-water, and the mixture is neutralized with potassium carbonate and extracted with chloroform. The extract is washed with an aqueous solution of sodium chloride and dried over magnesium sulfate. After the solvent is distilled off under reduced pressure, the residue is purified by silica gel chromatography (chloroform:methanol = 10:1) and recrystallized from chloroform methanol to give 2.7 g of 8-hydroxy-2-(2-pyridyl)-4,4a,5,6-tetrahydrobenzo[h]cinnolin-3(2H)-one as white crystals, m.p. 193°-194° C.

The starting 8-methoxy compounds can be obtained in the following manner.

A mixture of 20 g of 6-methoxy-1-oxo-1,2,3,4-tetrahydronaphthalene-2-acetic acid, 10.9 g of 2-hydrazinopyridine and 150 ml of ethanol is heated under reflux for 2 hours. The resulting crystals are collected, whereto 50 ml of acetic acid is added. The mixture is heated under reflux for 30 minutes. Acetic acid is distilled off under reduced pressure, and water is added to the residue. The resultant crystals are collected and recrystallized from chloroform - ethanol to give 21.5 g of 8-methoxy-2-(2-pyridyl)-4,4a,5,6-tetrahydrobenzo[h]cinnolin-3(2H)-one as white crystals, m.p. 194°–196° C.

REFERENCE EXAMPLE 3

A mixture of 5 g of 9-fluoro-2-(4-hydroxyphenyl)-5,6-dihydrobenzo[h]cinnolin-3(2H)-one, 4.5 g of chloroacetone, 8.8 g of potassium carbonate and 100 ml of acetone is heated under reflux for 9 hours. After acetone is distilled off, water and isopropyl ether are added to the residue. The resultant crystals are collected and washed with ethanol to give 5 g of crude 9-fluoro-2-[4-(2-oxopropoxy)phenyl]-5,6-dihydrobenzo[h]cinnolin-3(2H)-one, which is subjected to the following reaction without purification.

In the same manner, 9-fluoro-2-[4-(2-oxopropoxy)phenyl]-4,4a,5,6-tetrahydrobenzo[h]cinnolin-3(2H)-one (m.p. 195°–196° C.) and 2-[4-(2-oxopropoxy)phenyl]-2,3,4,4a-tetrahydro-5H-(1)benzothiopyrano[4,3-c]pyridazin-3-one (m.p. 177°–180° C.) can be obtained.

EXAMPLE 1

To 100 ml of ethanol is added 2-(4-hydroxyphenyl)-9-methyl-4,4a,5,6-tetrahydrobenzo[h]cinnolin-3(2H)-one, and 1 g of 85% potassium hydroxide is added to the mixture while stirring at room temperature. After 2.5 g of 1-(3-chloropropyl)piperidine is added thereto, the mixture is heated under reflux for 11 hours.

The reaction mixture is filtered, and the filtrate is concentrated under reduced pressure. The residue is extracted with chloroform. The extract is washed with water and dried over anhydrous magnesium sulfate. The solvent is distilled off under reduced pressure to give 7.5 g of a brown oily substance. This oily substance is subjected to column chromatography, followed by conversion into its maleate to give 2.9 g of 9-methyl-2-[4-(3-piperidinopropoxy)phenyl]-4,4a,5,6-tetrahydrobenzo[h]cinnolin-3(2H)-one.maleate, m.p. 171°–172° C.

EXAMPLE 2

To 50 ml of methanol is added 9 g of 9-fluoro-2-(4-hydroxyphenyl)-4,4a,5,6-tetrahydrobenzo[h]cinnolin-3(2H)-one, and 1.7 g of sodium hydroxide dissolved in 70 ml of methanol is added to the mixture under stirring at room temperature. Thereto is added 13 g of epichlorohydrin, and the mixture is heated under reflux for 2 hours. After the reaction mixture is filtered, the filtrate is concentrated under reduced pressure and the residue is extracted with chloroform. The extract is washed with water and dried over anhydrous magnesium sulfate. Thereafter, the solvent is distilled off to give 12.5 g of a brown oily substance. This oily substance is subjected to column chromatography. Isopropyl ether is added to the resulting crystals, and the crystals are collected by filtration to give 4 g of 2-[4-(2,3-epoxypropoxy)phenyl]-9-fluoro-4,4a,5,6-tetrahydrobenzo[h]cinnolin-3(2H)-one as white crystals, m.p. 128°–130° C.

To 30 ml of dimethylformamide is added 3 g of 2-[4-(2,3-epoxypropoxy)phenyl]-9-fluoro-4,4a,5,6-hexahydrobenzo[h]cinnoline-3(2H)-one, and 12 g of isopropylamine is added thereto under stirring at room temperature. The mixture is stirred under heating at 30°–50° C. for 14 hours. After the completion of the reaction, the solvent is distilled off under reduced pressure and the residue is extracted with chloroform. After the extract is washed with water and dried over anhydrous magnesium sulfate, the solvent is distilled off. The obtained crystals are converted into its maleate to give 2.3 g of 9-fluoro-2-[4-(2-hydroxy-3-isopropylaminopropoxy)phenyl]-4,4a,5,6-tetrahydrobenzo[h]cinnolin-3(2H)-one. maleate, m.p. 193°–195° C.

EXAMPLE 3

To 60 ml of dried dimethylformamide is added 5 g of 9-hydroxy-2-(4-hydroxyphenyl)-4,4a,5,6-tetrahydrobenzo[h]cinnolin-3(2H)-one, and thereto is added 1.6 g of 60% sodium hydroxide. After the mixture is stirred at room temperature for 1 hour, 5 g of 3-dimethylaminopropyl chloride is added thereto. The mixture is stirred under heating at 60°–70° C. for 14 hours. After the completion of the reaction, the solvent is distilled off and the residue is extracted with chloroform. The extract is washed with water and dried over anhydrous magnesium sulfate. Thereafter, the solvent is distilled off. The obtained oily substance (7.8 g) is subjected to column chromatography to give 5.2 g of 2-[4-(3-dimethylaminopropoxy)phenyl]-9-(3-dimethylaminopropoxy)-4,4a,5,6-tetrahydrobenzoh]cinnolin-3(2H)-one as an oily substance.

To 50 ml of acetone is dissolved 5.0 g of the above-obtained substance, and 3.3 g of methyl iodide is added to the solution while stirring at room temperature. The mixture is stirred under reflux for 10 minutes. After the completion of the reaction, the solvent is distilled off and methanol is added to the residue and the deposited crystals are collected by filtration. The obtained crystals are recrystallized from a mixed solvent of methanol and isopropyl ether to give 2.1 g of 2-[4-(3-trimethylammoniopropoxy)phenyl]-9-(3-trimethylammoniopropoxy)-4,4a,5,6-tetrahydrobenzo[h]cinnolin-3(2H)-one.diiodide.hemihydrate as yellow crystals, m.p. 222°–225° C. (decomposition).

EXAMPLE 4

To 60 ml of dry dimethylformamide is added 6.1 g of 9-hydroxy-2-(4-methylphenyl)-4,4a,5,6-tetrahydrobenzo[h]cinnolin-3(2H)-one, and 0.96 g of 60% sodium hydride is added thereto while stirring at room temperature. After stirring at room temperature for 1 hour, 2.8 g of 3-dimethylaminopropyl chloride is added to the mixture. After the mixture is stirred over water bath under heating at 40°–50° C. for 5 hours, the reaction mixture is poured into a large amount of water, followed by extraction with chloroform. The organic layer is washed with water and dried over anhydrous magnesium sulfate. Then, the solvent is distilled off. The residue is subjected to column chromatography and the eluate is converted into its maleate, which is recrystallized from a mixed solvent of methanol and isopropyl ether to give 7.2 g of 9-(3-dimethylaminopropoxy)-2-(4-methylphenyl)-4,4a,5,6-tetrahydrobenzo[h]cinnolin-3(2H)-one.maleate, m.p. 159°–162° C.

EXAMPLE 5

To 50 ml of dry dimethylformamide is added 4.5 g of 2-(4-chlorophenyl)-9-hydroxy-2,3,4,4a-tetrahydro-5H-(1)benzothiopyrano[4,3-c]pyridazin-3-one, and 0.7 g of 60% sodium hydride is added thereto while stirring at room temperature. After stirring at room temperature for 1 hour and addition of 2 g of 3-dimethylaminopropyl chloride, the mixture is stirred under heating at 40°-50° C. for 3 hours. After the completion of the reaction, the reaction mixture is poured into a large amount of water and the mixture is extracted with chloroform. The extract is washed with water and dried over anhydrous magnesium sulfate. Thereafter, the solvent is distilled off. The residue is subjected to column chromatography and the eluate is converted into its fumarate to give 0.52 g of 2-(4-chlorophenyl)-9-(3-dimethylaminopropoxy)-2,3,4,4a-tetrahydro-5H-(1)benzothiopyrano[4,3-c]pyridazin-3-one.fumarate, as yellow crystals, m.p. 208°-210° C.

EXAMPLE 6

To 150 ml of methanol is added 15.5 g of 2-(4-hydroxyphenyl)-2,3,4,4a-tetrahydro-5H-(1)benzothiopyrano[4,3-c]-pyridazin-3-one, and a solution of 2.6 g of sodium hydroxide in 150 ml methanol is added thereto while stirring at room temperature. To the mixture is added 14 g of epichlorohydrin, under heating at 50°-60° C. for 8 and the mixture is stirred hours. Thereafter the solvent is distilled off. To the residue is added a 10% aqueous solution of sodium hydroxide, followed by extraction with chloroform. The extract is washed with water and dried over anhydrous magnesium sulfate. After the solvent is distilled off, the residue is subjected to column chromatography to give 10.6 g of 2-[4-(2,3-epoxypropoxy)phenyl]-2,3,4,4a-tetrahydro-5H-(1)benzothiopyrano-[4,3-c]pyridazin-3-one as an oily substance.

This oily substance (2.7 g) is dissolved in 10 ml of dimethylformamide and 0.71 g of morpholine is added to the solution. The mixture is heated over a water bath at 70° C. for 3 hours. After the completion of the reaction, the solvent is distilled off and the residue is dissolved in chloroform. The solution is washed with water and dried over anhydrous magnesium sulfate. After the solvent is distilled off, 23% hydrochloric acid in isopropyl alcohol is added to the residue. The solvent is distilled off, followed by addition of ethanol and isopropyl ether. The resultant crystals are collected by filtration, washed with hot ethanol and recrystallized from a mixed solvent of methanol and isopropyl ether to give 2 g of 2-[4-(2-hydroxy-3-morpholinopropoxy)-phenyl]-2,3,4,4a-tetrahydro-5H-(1)benzothiopyrano-[4,3-c]pridazin-3-one.hydrochloride, as white crystals, m.p. 136°-140° C. (decomposition).

EXAMPLE 7

To a mixture of 37 g of 9-fluoro-2-[4-(2-oxopropoxy)-phenyl]-5,6-dihydrobenzo[h]cinnolin-3(2H)-one, 33 g of dimethylamine hydrochloride and 700 ml of ethanol is added dropwise 200 ml of an ethanol solution of 10 g of sodium cyanoboron hydride while stirring under heating and reflux over the period of 2 hours. After the completion of the dropwise addition, the reaction is concentrated under reduced pressure. To the residue is added 200 ml of water, and then conc. hydrochloric acid is added thereto under ice-cooling. After the mixture is stirred at room temperature for 1 hour, it is rendered alkaline with potassium carbonate and extracted with ethyl acetate. After the extract is washed with water and dried over magnesium sulfate, the solvent is distilled off under reduced pressure Ethanol is added to the thus obtained oily substance and further fumaric acid is added thereto to convert into its salt. The resultant crystals are recrystallized from hydrous ethanol to give 9-fluoro-2-[4-(2-dimethylaminopropoxy)phenyl]-5,6-dihydrobenzo[h]cinnolin-3(2H)-one.fumarate.

EXAMPLE 8

To a mixture of 116 g of 9-fluoro-2-[4-(2-dimethylaminopropoxy)phenyl]-4,4a,5,6-tetrahydrobenzo[h]cinnolin-3(2H)-one and 1.2 l of acetic acid is added 116 ml of 30% hydrobromic acid—acetic acid. While the solution is heated to 50° C., a solution of 48 g of hydrobromic acid and 200 ml of acetic acid is added dropwise over the period of 30 minutes. After the completion of the dropwise addition, the mixture is stirred for further 30 minutes. The solvent is distilled off under reduced pressure. Water and ethyl acetate are added to the residue, and the mixture is rendered alkaline with potassium carbonate. The ethyl acetate layer is separated, washed with water and extracted with an aqueous solution of hydrochloric acid. The hydrochloric acid layer is rendered alkaline with potassium carbonate, and the resultant oily substance is dissolved in ethyl acetate, which is washed with water and dried over magnesium sulfate. The solvent is distilled off under reduced pressure. Ethanol and fumaric acid are added to the residue to convert it into its salt. The resultant crystals are collected by filtration and recrystallized from water—ethanol to give 9-fluoro-2-[4-(2-dimethylaminopropoxy)phenyl]-5,6-dihydrobenzo[h]cinnolin-3(2H)-one.fumarate, m.p. 178°-180° C.

EXAMPLE 9

By conducting reactions and treatments in the same manner as in Example 1 using 9-fluoro-2-(4-hydroxyphenyl)-4,4a,5,6-tetrahydrobenzo[h]cinnolin-3(2H)-one and 3-dimethylaminopropyl chloride, there is obtained 9-fluoro-2-[4-(3-dimethylaminopropoxy)phenyl]-4,4a,5,6-tetrahydrobenzo[h]cinnolin-3(2H)-one, m.p. 118°-120° C.

EXAMPLE 10

A mixture of 9.3 g of 9-fluoro-2-(4-hydroxyphenyl)-4,4a,5,6-tetrahydrobenzo[h]cinnolin-3(2H)-one, 100 ml of acetone, 8.3 g of potassium carbonate and 7.5 g of chloropropionaldehydediethylacetal is stirred under heating and reflux for 5 hours. After the completion of the stirring, the solvent is distilled off under reduced pressure. Water is added to the residue and the mixture is extracted with chloroform and dried over magnesium sulfate, followed by concentration under reduced pressure to give crude 9-fluoro-2-[4-(3-diethoxypropoxy)-phenyl]-4,4a,5,6-tetrahydrobenzo[h]cinnolin-3(2H)-one. This compound (8.2 g) is suspended in 100 ml of methanol, and while stirring at room temperature, 10 ml of 1N hydrochloric acid is added to the suspension. After stirring at room temperature for 1 hour, the solvent is distilled off under reduced pressure. After addition of chloroform to the residue, the mixture is washed with water, dried over magnesium sulfate and concentrated. To the residue are added 100 ml of ethanol and 2.5 g of dimethylamine hydrochloride, and 1.9 g of sodium cyanoboron hydride is added to the mixture while stirring at room temperature. After stirring at room temperature for 15 hours, the solvent is distilled off under reduced pressure. Water is added to the residue, and the mixture is extracted with chloroform. The extract is washed with water, dried over magnesium sulfate and concentrated to give an oily substance. The thus-obtained oily substance is subjected to silica gel column chromatography and the objective fractions are recrystallized from isopropyl alcohol to give 9-fluoro-2-(4-dimethylaminopropoxyphenyl)-4,4a,5,6-tetrahydrobenzo[h]cinnolin-3(2H)-one, m.p. 118°–120° C.

EXAMPLE 11

By conducting reactions and treatments in the same manner as in Example 1 using 9-fluoro-2-(4-hydroxyphenyl)-4,4a,5,6-tetrahydrobenzo[h]cinnolin-3(2H)-one and 1-methyl-2-dimethylaminoethyl chloride, there are obtained crude crystals, which are subjected to silica gel column chromatography. The crystals obtained from fractions at earlier stage are converted into fumarate, followed by recrystallization from ethanol to give 9-fluoro-2-[4-(1-methyl-2-dimethylaminoethoxy)-phenyl]-4,4a,5,6-tetrahydrobenzo[h]cinnolin-3(2H)-one.fumarate.½ hydrate [referred to as compound of Example 11a], m.p. 176°–179° C. (decomposition). The crystals obtained from fractions at later stage are converted into fumarate, which is recrystallized from water to give 9-fluoro-2-[4-(2-dimethylaminopropoxy)-phenyl]-4,4a,5,6-tetrahydrobenzo[h]cinnolin-3(2H)-one.fumarate [referred to as compound of Example 11b], m.p. 194°–195° C.

EXAMPLE 12

By conducting reactions and treatments in the same manner as in Example 1 using 9-fluoro-2-(4-hydroxyphenyl)-4,4a,5,6-tetrahydrobenzo[h]cinnolin-3(2H)-one and 2-dimethylaminoethyl chloride, obtained is 9-fluoro-2-[4-(2-dimethylaminoethoxy)phenyl]-4,4a,5,6-tetrahydrobenzo[h]cinnolin-3(2H)-one.fumarate, m.p. 194°–195° C. (decomposition).

EXAMPLE 13

By conducting reactions and treatments in the same manner as in Example 1 using 2-(2-hydroxyphenyl)-4,4a,5,6-tetrahydrobenzo[h]cinnolin-3(2H)-one and 3-dimethylaminopropyl chloride, obtained is 2-[2-(3-dimethylaminopropoxy)phenyl]-4,4a,5,6-tetrahydrobenzo[h]cinnolin-3(2H)-one.fumarate, m.p. 194°–195° C. (decomposition).

EXAMPLE 14

By conducting reactions and treatments in the same manner as in Example 2 using 9-fluoro-2-(2-hydroxyphenyl)-4,4a,5,6-tetrahydrobenzo[h]cinnolin-3(2H)-one in place of 9-fluoro-2-(4-hydroxyphenyl)-4,4a,5,6-tetrahydrobenzo[h]cinnolin-3(2H)-one in Example 2, obtained is 9-fluoro-2-[2-(2-hydroxy-3-isopropylaminopropoxy)phenyl]-4,4a,5,6-tetrahydrobenzo[h]cinnolin-3(2H)-one.maleate, m.p. 157°–158° C.

EXAMPLE 15

By conducting reactions and treatments in the same manner as in Example 1 using 9-fluoro-2-(3-hydroxyphenyl)-4,4a,5,6-tetrahydrobenzo[h]cinnolin-3(2H)-one in place of 2-(4-hydroxyphenyl)-9-methyl-4,4a,5,6-tetrahydrobenzo[h]cinnolin-3(2H)-one in Example 1 and 3-dimethylaminopropyl chloride in place of 1-(3-chloropropyl)piperidine, obtained is 9-fluoro-2-[3(3-dimethylaminopropoxy)phenyl]-4,4a,5,6-tetrahydrobenzo[h]cinnolin-3(2H)-one, m.p. 98°–99° C.

EXAMPLE 16

By conducting reactions and treatments in the same manner as in Example 1 using 9-fluoro-2-(4-hydroxyphenyl)-4,4a,5,6-tetrahydrobenzo[h]cinnolin-3(2H)-one and 2-diethylaminoethyl chloride and converting into hydrochloride, obtained is 9-fluoro-2-[4-(2-diethylaminoethoxy)phenyl]-4,4a,5,6-tetrahydrobenzo[h]cinnolin-3(2H)-one.hydrochloride.monohydrate, m.p. 145°–149° C.

EXAMPLE 17

By conducting reactions and treatments in the same manner as in Example 12 using 9-fluoro-2-(3-hydroxyphenyl)-4,4a,5,6-tetrahydrobenzo[h]cinnolin-3(2H)-one in place of 9-fluoro-2-(4-hydroxyphenyl)-4,4a,5,6-tetrahydrobenzo[h]cinnoline-3(2H)-one in Example 12 with 2-diethylaminoethyl chloride, obtained is 9-fluoro-2-[3-(2-diethylaminoethoxy)phenyl]-4,4a,5,6-tetrahydrobenzo[h]cinnolin-3(2H)-one maleate, m.p. 151°–153° C.

EXAMPLE 18

By conducting reactions and treatments in the same manner as in Example 4 using 3-morpholinopropyl chloride instead of 3-dimethylaminopropyl chloride in Example 4, obtained is 2-(4-methylphenyl)-9-(3-morpholinopropoxy)-4,4a,5,6-tetrahydrobenzo[h]cinnolin-3(2H)-one.hydrochloride.hemihydrate, m.p. 117°–120° C.

EXAMPLE 19

By conducting reactions and treatments in the same manner as in Example 4 using 8-hydroxy-2-(4-methylphenyl)-8-hydroxy-4,4a,5,6-tetrahydrobenzo[h]cinnolin-3(2H)-one in place of 9-hydroxy-2-(4-methylphenyl)-4,4a,5,6-tetrahydrobenzo[h]cinnolin-3(2H)-one with 3-morpholinopropyl chloride, obtained is 2-(4-methylphenyl)-8-(3-morpholinopropoxy)-4,4a,5,6-tetrahydrobenzo[h]cinnolin-3(2H)-one.hydrochloride.hemihydrate,
m.p. 198°–200° C. (decomposition).

EXAMPLE 20

By conducting reactions and treatments in the same manner as in Example 19 using 8-hydroxy-2-(3-methylphenyl)-4,4a,5,6-tetrahydrobenzo[h]cinnolin-3(2H)-one instead of 8-hydroxy-2-(4-methylphenyl)-4,4a,5,6-tetrahydrobenzo[h]cinnolin-3(2H)-one in Example 19, obtained is 2-(3-methylphenyl)-8-(3-morpholinopropoxy)-4,4a,5,6-tetrahydrobenzo[h]cinnolin-3(2H)-one, m.p. 113°–114° C.

EXAMPLE 21

By conducting reactions and treatments in the same manner as in Example 9 using 2-methyl-3-dimethylaminopropyl chloride in place of 3-dimethylaminopropyl chloride in Example 9, obtained is 9-fluoro-2-[4-(2-methyl-3-dimethylaminopropoxy)phenyl]-4,4a,5,6-tetrahydrobenzo[h]cinnolin-3(2H)-one.hydrochloride, m.p. 205°–206° C.

EXAMPLE 22

By conducting reactions and treatments in the same manner as in Example 9 using 9-fluoro-2-(3-hydroxyphenyl)-4,4a,5,6-tetrahydrobenzo[h]cinnoline-3(2H)-one in place of 9-fluoro-2-(4-hydroxyphenyl)-4,4a,5,6-tetrahydrobenzo[h]cinnoline-3(2H)-one in Example 9 and 2-methyl-3-dimethylaminopropyl chloride in place of 3-dimethylaminopropyl chloride, obtained is 9-fluoro-2-[3-(2-methyl-3-dimethylaminopropoxy)-phenyl]-4,4a,5,6-tetrahydrobenzo[h]cinnolin-3(2H)-one.fumarate. monohydrate, m.p. 209°–210° C.

EXAMPLE 23

By conducting reactions and treatments in the same manner as in Example 9 using 3-morpholinopropyl chloride in place of 3-dimethylaminopropyl chloride in Example 9, obtained is 9-fluoro-2-[4-(3-morpholinopropoxy)phenyl]-4,4a,5,6-tetrahydrobenzo[h]cinnolin-3(2H)-one.hydrochloride.hemihydrate, m.p. 173°–1.75° C. (decomposition).

EXAMPLE 24

By conducting reactions and treatments in the same manner as in Example 16 using 2-(4-hydroxyphenyl)-2,3,4,4a-tetrahydro-5H-(1)benzothiopyrano[4,3-c]pyridazin-3-one in place of 9-fluoro-2-(4-hydroxyphenyl)-4,4a,5,6-tetrahydrobenzo[h]cinnolin-3(2H)-one in Example 16, obtained is 2-[4-(2-diethylaminoethoxy)phenyl]-2,3,4,4a-tetrahydro-5H-(1)benzothiopyrano[4,3-c]-pyridazin-3-one.fumarate, m.p. 160°–163° C. (decomposition).

EXAMPLE 25

By conducting reactions and treatments in the same manner as in Example 24, using 2-(4-hydroxyphenyl)-2,3,4,4a-tetrahydro-5H-(1)benzothiopyrano[4,3-c]pyridazin-3-one and 3-dimethylaminopropyl chloride, obtained is 2-[4-(3-dimethylaminopropoxy)phenyl]-2,3,4,4a-tetrahydro-5H-(1)benzopyrano[4,3-c]pyridazin-3-one.fumarate, m.p. 216°–218° C. (decomposition).

EXAMPLE 26

By conducting reactions and treatments in the same manner as in Example 11 using 8,9-dimethyl-2-(4-hydroxyphenyl)-4,4a,5,6-tetrahydrobenzo[h]cinnolin-3(2H)-one and 1-methyl-2-dimethylaminoethyl chloride, converting into the maleate and recrystallizing, obtained is 8,9-dimethyl-2-[4-(2-dimethylaminopropoxy)phenyl]-4,4a,5,6-tetrahydrobenzo[h]cinnolin-3(2H)-one.maleate, m.p. 232°–235° C. (decomposition).

EXAMPLE 27

By conducting reactions and treatments in the same manner as in Example 1 using 8,9-dimethyl-2-(4-hydroxyphenyl)-4,4a,5,6-tetrahydrobenzo[h]cinnolin-3(2H)-one and 2-methyl-3-dimethylaminopropyl chloride and converting into the fumarate, obtained is 8,9-dimethyl-2-[4-(2-methyl-3-dimethylaminopropoxy)phenyl]-4,4a,5,6-tetrahydrobenzo[h]cinnolin-3(2H)-one. fumarate, m.p. 207°–209° C. (decomposition).

EXAMPLE 28

By conducting reactions and treatments in the same manner as in Example 1 using 9-fluoro-2-(4-hydroxyphenyl)-4,4a,5,6-tetrahydrobenzo[h]cinnolin-3(2H)-one and 1-methyl-2-dimethyl-aminoethyl chloride and converting into the fumarate, obtained is 9-fluoro-2-[4-(1-methyl-2-dimethylaminoethoxy)phenyl]-4,4a,5,6-tetrahydrobenzo[h]cinnolin-3(2H)-one.fumarate. hemihydrate, m.p. 176°–179° C. (decomposition).

EXAMPLE 29

By conducting reactions and treatments in the same as in Example 1 using 9-fluoro-2-(4-hydroxyphenyl)-5,6-dihydrobenzo[h]cinnolin-3(2H)-one and 1-methyl-2-dimethylaminoethyl chloride and converting into the fumarate, obtained is 9-fluoro-2-[4-(1-methyl-2-dimethylaminoethoxy)phenyl]-5,6-dihydrobenzo[h]cinnolin-3(2H)-one fumarate, m.p. 172°–174° C. (decomposition).

EXAMPLE 30

By conducting reactions and treatments in the same manner as in Example 7 using 9-fluoro-2-[4-(2-oxopropoxy)phenyl]-4,4a,5,6-tetrahydrobenzo[h]cinnolin-3(2H)-one and dimethylamine hydrochloride, obtained is 9-fluoro-2-[4-(2-dimethylaminopropoxy)phenyl]-4,4a,5,6-tetrahydrobenzo[h]cinnolin-3(2H)-one.fumarate, m.p. 194°–195° C. (decomposition).

EXAMPLE 31

By conducting reactions and treatments in the same manner as in Example 7 using 9-fluoro-2-[4-(2-oxopropoxy)phenyl]-4,4a,5,6-tetrahydrobenzo[h]cinnolin-3(2H)-one and methylamine, obtained is 9-fluoro-2-[4-(2-methylaminopropoxy)phenyl]-4,4a,5,6-tetrahydrobenzo[h]cinnolin-3(2H)-one.hemifumarate, m.p. 218°–220° C. (decomposition).

EXAMPLE 32

By conducting reactions and treatments in the same manner as in Example 7 using methylamine instead of dimethylamine hydrochloride in Example 7, obtained is 9-fluoro-2-[4-(2-methylaminopropoxy)phenyl]-5,6-dihydrobenzo[h]cinnolin-3(2H)-one.hemifumarate, m.p. 217°–219° C. (decomposition).

EXAMPLE 33

By conducting reactions and treatments in the same manner as in Example 7 using 9-chloro-2-[4-(2-oxopropoxy)phenyl]-4,4a,5,6-tetrahydrobenzo[h]cinnolin-3(2H)-one and dimethylamine hydrochloride, obtained is 9-chloro-2-[4-(2-dimethylaminopropoxy)phenyl]-4,4a,5,6-tetrahydrobenzo[h]cinnolin-3(2H)-one.fumarate, m.p. 189°–191° C. (decomposition).

EXAMPLE 34

By conducting reactions and treatments in the same manner as in Example 1 using 9-fluoro-2-(4-hydroxyphenyl)-5,6-dihydrobenzo[h]cinnolin-3(2H)-one and 1-methyl-2-dimethylaminoethyl chloride, obtained is 9-fluoro-2-[4-(2-dimethylaminopropoxy)phenyl]-5,6-dihydrobenzo[h]cinnolin-3(2H)-one.

EXAMPLE 35

By reacting the compound as obtained in Example 11 with 1-methyl-2-dimethylaminoethyl chloride and reacting and treating in the same manner as in Example 3, obtained is 9-fluoro-2-[4-(1-methyl-2-trimethylammonioethoxy)phenyl]-4,4a,5,6-tetrahydrobenzo[h]cinnolin-3(2H)-one·iodide.

EXAMPLE 36

By reacting with 1-methyl-2-dimethylaminoethyl chloride and treating in the same manner as in Example 1 using the 6-oxide compound corresponding to 2-(4-hydroxyphenyl)-2,3,4,4a-tetrahydro-5H-(1)benzothiopyrano[4,3-c]pyridazin-3-one in Example 6, obtained is 2-[4-(1-methyl-2-dimethylaminoethoxy)phenyl]-2,3,4,4a-tetrahydro-5H-(1)benzothiopyrano[4,3-c]-pyridazin-3-one.6-oxide.

EXAMPLE 37

By conducting reactions and treatments in the same manner as in Example 36 using the corresponding 6,6-dioxide compound instead of the 6-oxide compound in Example 36, obtained is 2-[4-(1-methyl-2-dimethylaminoethoxy)phenyl]-2,3,4,4a-tetrahydro-5H-(1)benzothiopyrano[4,3-c]pyridazin-3-one.6,6-dioxide.

EXAMPLE 38

By conducting reactions and treatments in the same manner as in Example 1 using 2-(4-hydroxyphenyl)-9-methyl-2,3,4,4a-tetrahydro-5H-(1)benzothiopyrano[4,3-c]pyridazin-3-one instead of 2-(4-hydroxyphenyl)-9-methyl-4,4a,5,6-tetrahydrobenzo[h]cinnolin-3(2H)-one in Example 1 and 1-methyl-2-dimethylaminoethyl chloride instead of 1-(3-chloromethyl)piperidine in Example 1, obtained is 9-methyl-2-[4-(1-methyl-2-dimethylaminoethoxy)phenyl]-2,3,4,4a-tetrahydro-5H-(1)benzothiopyrano[4,3-c]pyridazin-3-one.

EXAMPLE 39

By conducting reactions and treatments in the same manner as in Example 38 using 2-methyl-3-dimethylaminopropyl chloride instead of 1-methyl-2-dimethylaminoethyl chloride in Example 38, obtained is 9-methyl-2-[4-(2-methyl-3-dimethylaminopropoxy)phenyl]-2,3,4,4a-tetrahydro-5H-(1)benzothiopyrano-[4,3-c]pyridazin-3-one.

EXAMPLE 40

To a mixture of 1.4 g of 8-hydroxy-2-(2-pyridyl)-4,4a,5,6-tetrahydrobenzo[h]cinnolin-3(2H)-one, 1.4 g of potassium carbonate and 30 ml of dimethylformamide is added 1.3 g of N-(3-chloropropyl)morpholine, and the mixture is stirred at 55° C. for 3 hours. After the completion of the reaction, water is added to the reaction mixture and the mixture is extracted with ethyl acetate. The extract is washed with water and dried over magnesium sulfate. The solvent is distilled off under reduced pressure. The obtained oily substance is purified by silica gel column chromatography (chloroform : methanol = 10 : 1) and converted into the hydrochloride in methanol, which is recrystallized from methanol to give 0.6 g of 8-(3-morpholinopropoxy)-2-(2-pyridyl)-4,4a,5,6-tetrahydrobenzo[h]cinnolin-3(2H)-one. dihydrochloride.dihydrate as white crystals, m.p. 201°–202° C. (decomposition).

EXAMPLE 41

To a mixture of 3.6 g of 2-[4-(2-oxopropoxy)phenyl]-2,3,4,4a-tetrahydro-5H-(1)benzothiopyrano[4,3-c]pyridazin-3-one, 3.3 g of dimethylamine hydrochloride and 50 ml of ethanol is added dropwise 20 ml of a solution of 1 g of sodium cyanoboron hydride in 20 ml of ethanol while stirring under heating and reflux over 1 hour. The mixture is stirred under heating and reflux for further 4 hours. After the completion of the reaction, the solvent is distilled off, and water and dilute hydrochloric acid are added to the residue. After the mixture is left standing still for 30 minutes, it is neutralized with potassium carbonate and extracted with chloroform. The extract is dried over magnesium sulfate, and the solvent is distilled off. The residue is purified by silica gel column chromatography (chloroform:methanol = 10:1 ) and then converted into the fumarate in acetone, which is recrystallized from ethanol to give 3.4 g of 2-[4-(2-dimethylaminopropoxy)phenyl]-2,3,4,4a-tetrahydro-5H-(1)benzothiopyrano[4,3-c]pyridazin-3-one.fumarate as white crystals, m.p. 171°–173° C.

PHARMACEUTICAL FORMULATION EXAMPLE 1

| Injections (1 mg/2 ml) | |
|---|---|
| Formulation | |
| Compound of Example 7 | 0.05% |
| Sodium chloride | 0.9% |
| (Distilled water for injections is added in such an amount as to render the total amount 100.0%) | |

Production method

Bulk and sodium chloride are dissolved in injectable distilled water. The solution is filtered with membrane filter (of pore diameter of 0.2 μm). The amples are filled with 2 ml of the solution per ample and heat-sealed under nitrogen gas atmosphere.

The amples are subjected to high pressure vapor-sterilization at 115° C. for 30 minutes. They are put in shaded vessels to provide injections.

PHARMACEUTICAL FORMULATION EXAMPLE 2

| Tablets containing 10 mg of bulk per tablet (in total amount of 129 mg/tablet) | |
|---|---|
| Formulation of Plain Tablets | |
| Compound of Example 7 | 10.0 mg |
| Lactose | 51.5 mg |
| Corn starch | 20.0 mg |
| Crystalline cellulose | 30.0 mg |
| Polyvinylpyrrolidone K-30 | 5.0 mg |
| Talc | 3.0 mg |
| Magnesium stearate | 0.5 mg |
| Formulation of coating agents | |
| Hydroxypropylmethylcellulose 2910 | 4.5 mg |
| Polyethylene glycol 6000 | 0.9 mg |
| Titanium oxide | 2.7 mg |
| Talc | 0.9 mg |

Production method

Bulk, lactose, corn starch and crystalline cellulose are mixed and kneaded with the use of an aqueous solution of polyvinylpyrrolidone K-30. The mixture is passed through a sieve of 16 mesh and formed into particles.

After the obtained particles are dried with heat air circulation type drier at 50° C. for 2 hours, they are passed through a sieve of 24 mesh. The obtained particles are mixed with talc and magnesium stearate and the mixture is tableted into 120 mg-tablets with a pounder with the diameter of 7 mm.

Further, coating is conducted with hydroxypropylmethyl cellulose 2910, polyethylene glycol 6000, titanium oxide and talc in accordance with the conventional method to give tablets.

Below, pharmacological Experimental Examples of the present invention are specifically shown.

EXPERIMENTAL EXAMPLE 1

Stimulating Effects on Phagocytosis of Leukocytes

In accordance with the method by Stossel [Journal of Clinical Investigation, vol. 51, p. 615 (1972)], the experiment was conducted. Thus, glycogen was intraperitoneally administered to ICR mice weighing 30–35 g, and 3 hours after administration, leukocytes in abdominal cavity were collected. A suspension containing leukocytes at $5 \times 10^6$ leukocytes/ml was prepared. To a 200

μl of the suspension were added test compounds, 100 μl of mouse serum and 100 μl of non-viable yeasts ($1 \times 10^8$ yeasts/ml). The mixture was cultivated at 37° C. for 20 minutes. By observing some 200 leukocytes of the reaction mixture with microscope (by magnification of 400), the number of the leukocytes which phagocytized at least one non-viable yeast was countered. The ratio of the number of phagocytic leukocytes treated with 1 mM of the test compounds relative to that of phagocytic leukocytes of controls was estimated by the percentage. The results are shown in Table 1.

EXPERIMENTAL EXAMPLE 2

Stimulating Effects on Phagocytosis of Macrophages

Casein.sodium was intraperitoneally administered to rats, and 3–4 days after the administration, macrophages were intraperitoneally collected. The phagocytosis was estimated in the same manner as in Experimental Example 1. The reaction conditions were the same except that macrophages were used instead of leukocytes. The results are shown in Table 1

TABLE 1

| Test compound (Example No.) | Phagocytosis of leukocyte (%) | Phagocytosis of macrophages (%) |
| --- | --- | --- |
| 2 | 148 | 196 |
| 7 | 195 | 212 |
| 9 | 162 | 168 |
| 11b | 315 | 182 |
| 15 | 195 | 171 |
| 22 | 170 | 192 |
| 24 | 182 | 188 |
| 25 | 177 | 174 |
| 29 | 198 | 168 |
| 32 | 233 | 224 |

EXPERIMENTAL EXAMPLE 3

Restorative Effects on Leukopenia

ICR mice weighing 30–35 g were intraperitoneally administered at the dose of 200 mg/kg with cyclophosphamide, and the next day, the test compounds were orally administered at the dose of 0.3 mg/kg. On the 4th day after the administration of cyclophosphamide, leukocyte count in the peripheral blood of the mice was measured. The ratio of the number of peripheral leukocytes of mice treated with the test compounds relative to that of mice treated with cyclophosphamide alone was estimated by the percentage. The results are shown in Table 2.

TABLE 2

| Test compound (Example No.) | Restorative effects on leukopenia (%) |
| --- | --- |
| 2 | 149 |
| 7 | 174 |
| 9 | 163 |
| 11b | 189 |
| 15 | 188 |
| 22 | 153 |
| 29 | 178 |

EXPERIMENTAL EXAMPLE 4

Protective Effects against Infection in Leukopenia

Male ICR mice weighing 23–27 g aged 5 weeks were intraperitoneally administered with cyclophosphamide at the dose of 200 mg/kg, and 4 days after the administration, the *Escherichia coli* O-111 strains were subcutaneously inoculated to the mice at $1 \times 10^8$ CFU, which was taken as control groups. For the groups of mice to be treated with the drugs, the test compounds were subcutaneously administered to the mice for consecutive 3 days from the following day of the administration of cyclophosphamide (CY). Seven days after the inoculation of Escherichia coli, the survival rate of the groups treated with the drugs relative to that of the control groups was compared. The results are shown in Table 3.

TABLE 3

| Test compound (Example No.) | Dosage (mg/kg, subcutaneously) | Survival rate (%) | Survival rate (% of CY treatment) |
| --- | --- | --- | --- |
| 11b | 1 | 43 | 253 |
|  | 0.1 | 27 | 159 |
|  | 0.01 | 33 | 194 |

EXPERIMENTAL EXAMPLE 5

Protective Effects against Infection in Leukopenia

In the same manner as in Experimental Example 4, except that the Escherichia coli strains were intravenously inoculated to the mice at $5 \times 10^7$ CFU and the test compounds were also intravenously inoculated to the mice, the experiment was conducted and the survival rates were estimated.

TABLE 4

| Test compound (Example No.) | Dosage (mg/kg, intravenously) | Survival rate (%) | Survival rate (% of CY treatment) |
| --- | --- | --- | --- |
| 7 | 0.01 | 48.3 | 193 |
| 11b | 0.01 | 45.0 | 225 |

TOXICITY TEST

No occurence of death was observed when the compounds of Examples 7 and 11b were administered at the dose of 100 mg/kg (intravenously), 300 mg/kg (intraperitoneally) and 1000 mg/kg (orally).

From the results of the foregoing experiments, it has been shown that the compounds of the present invention possess excellent stimulating effects on phagocytosis of leukocytes and macrophages, restorative effects on leukopenia and protective effects against infection, and exhibit antitumor actions against IMC cancer and have extremely low toxicity. Thus, the compounds of the present invention stimulate the function of the reticuloendothelial system and activate immune responses, and therefore they can be administered to patients effectively and safely as the medicines for the prophylaxis and therapy of diseases accompanied by immuno-deficiency.

While the present invention has been in detail explained in the specification including working examples, particularly the working examples can be changed and modified in various ways within the spirit and scope of the present invention.

We claim:

1. A fused pyridazine compound of the formula

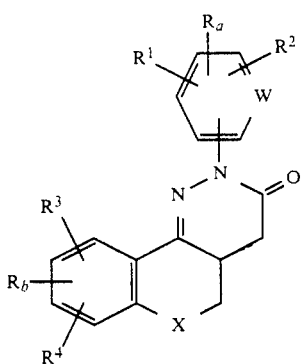

wherein $R^1$, $R^2$, $R^3$ and $R^4$ are the same or different and are respectively hydrogen, a halogen, hydroxy, nitro, amino, cyano, trifluoromethyl, a straight- or branched-chain $C_{1-8}$ alkyl, a straight- or branched-chain $C_{1-8}$ alkoxy or $C_{2-5}$ alkanoylamino; $R_a$ is a group of the formula

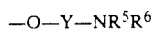

wherein $R^5$ and $R^6$, the same or different, are respectively hydrogen, a straight- or branched-chain $C_{1-8}$ alkyl or a phenyl-$C_{1-4}$ alkyl in which the alkyl moiety is a straight- or branched-chain or a substituted phenyl-$C_{1-4}$ alkyl having, on the phenyl ring, 1 to 3 substituent(s) selected from the group consisting of halogens, hydroxy, nitro, amino, cyano, trifluoromethyl, straight- or branched-chain $C_{1-8}$ alkyls, straight- or branched-chain $C_{1-8}$ alkoxys and $C_{2-5}$ alkanoylaminos or a group forming a 5- or 6-membered saturated heterocycle together with the adjacent nitrogen atom selected from the group consisting of 1-pyrrolidinyl, piperidino, morpholino, 1-piperazinyl, 4-substituted-1-piperazinyl wherein the substituent is a straight- or branched-chain $C_{1-8}$ alkyl, a hydroxy-$C_{1-8}$ alkyl, phenyl, a phenyl-$C_{1-4}$ alkyl, or a substituted phenyl-$C_{1-4}$ alkyl having, on the phenyl ring, 1 to 3 substituent(s) selected from halogens, hydroxy, nitro, amino, cyano, trifluoromethyl, straight- or branched-chain $C_{1-8}$ alkyls, straight- or branched-chain $C_{1-8}$ alkoxys and $C_{2-5}$ alkanoylaminos, and Y stands for a straight- or branched-chain $C_{1-8}$ alkylene which may have a hydroxy group as a substituent on the chain, and; W is =CH— or =N—; X is $CH_2$, S, SO, $SO_2$ or O; and the bond designated by a broken line represents a single bond or a double bond, or a pharmaceutically acceptable salt or hydrate thereof.

2. A compound or a pharmaceutically acceptable salt or hydrate thereof as claimed in claim 1 or claim 2 wherein X is $CH_2$ or S.

3. A compound or a pharmaceutically acceptable salt or hydrate thereof as claimed in claim 1 which is selected from a group consisting of 9-fluoro-2-[4-(2-dimethylaminopropoxy)phenyl]-5,6-dihydrobenzo[h]cinnolin-3(2H)-one, 9-fluoro-2-[4-(1-methyl-2-dimethylaminoethoxy)-phenyl]-4,4a,5,6-tetrahydrobenzo[h]cinnolin-3(2H)-one, 9-fluoro-2-[4-(2-methylaminopropoxy)phenyl]-5,6-dihydrobenzo[h]cinnolin-3(2H)-one, 9-fluoro-2-[4-(3-dimethylaminopropoxy)phenyl]-4,4a,5,6-tetrahydrobenzo[h]cinnolin-3(2H)-one, 2-[4-(3-dimethylaminopropoxy)phenyl]-2,3,4,4a-tetrahydro-5H-(1)benzothiopyrano[4,3-c]pyridazin-3-one, 9-fluoro-2-[3-(3-dimethylaminopropoxy)phenyl]-4,4a,5,6-tetrahydrobenzo[h]cinnolin-3(2H)-one, 9-fluoro-2-[3-(2-methyl-3-dimethylaminopropoxy)-phenyl]-4,4a,5,6-tetrahydrobenzo[h]cinnolin-3(2H)-one, 2-[4-(2-diethylaminoethoxy)phenyl]-2,3,4,4a-tetrahydro-5H-(1)benzothiopyrano[4,3-c]pyridazin-3-one and 9-fluoro-2-[4-(2-hydroxy-3-isopropylaminopropoxy)-phenyl]-4,4a,5,6-tetrahydrobenzo[h]cinnolin-3(2H)-one.

4. A pharmaceutical composition which comprises a compound of a pharmaceutically acceptable salt or hydrate thereof as claimed in claim 1, 2 or 3 and a pharmaceutically acceptable carrier.

* * * * *